United States Patent [19]
Konishi et al.

[11] Patent Number: 6,066,310
[45] Date of Patent: May 23, 2000

[54] DIAGNOSTIC AND THERAPEUTIC METHOD FOR TUMOR USING RADIOLABELED AVIDIN

[75] Inventors: Junji Konishi; Harumi Sakahara; Meili Zhang; Zhengsheng Yao, all of Kyoto, Japan

[73] Assignee: Nihon Medi-Physics Co., Ltd., Hygo-Ken, Japan

[21] Appl. No.: 09/074,593

[22] Filed: May 8, 1998

[30]     Foreign Application Priority Data

May 8, 1997  [JP]  Japan .................................... 9-134341

[51] Int. Cl.⁷ ............................... A61K 51/08; C07F 5/00
[52] U.S. Cl. ...................... 424/1.69; 424/1.73; 424/1.85; 534/10; 534/14
[58] Field of Search .................... 424/1.65, 1.69, 424/1.77, 1.81, 1.45, 9.3, 1.73, 1.85; 530/367, 396, 395; 514/8; 435/4.5; 534/10, 14

[56]           References Cited

U.S. PATENT DOCUMENTS

| | | | |
|---|---|---|---|
| 5,032,678 | 7/1991 | Washino et al. | 534/14 |
| 5,126,122 | 6/1992 | Chomant et al. | 424/1.69 |
| 5,135,736 | 8/1992 | Anderson et al. | 424/1.49 |
| 5,525,338 | 6/1996 | Goldenberg | 424/178.1 |
| 5,578,287 | 11/1996 | Theodore et al. | 424/1.49 |

FOREIGN PATENT DOCUMENTS 2124833   5/1990   Japan .
 623114   3/1994   Japan .

OTHER PUBLICATIONS

Hiller et al. (1978) Biochem.J. 246 (167–171).
Arano et al. (1994) J. Med. Chem. 34 (2609–2618).
Zalutsky et al. (1987) Appl.Radia.Isot. 38/12 (1051–1055).

*Primary Examiner*—José G. Dees
*Assistant Examiner*—Michael R. Hartley
*Attorney, Agent, or Firm*—Birch, Stewart, Kolasch & Birch, LLP

[57]           ABSTRACT

A method for diagnosis or therapeutics of tumor which is characterized by administering an amount of a glycoprotein having a molecule capable of specifically binding to a lectin to a subject in need of such diagnosis or treatment and use of the glycoprotein for the manufacture of a diagnostic and therapeutic agent useful in detection or therapeutics of tumor are disclosed.

4 Claims, 4 Drawing Sheets

DIAGNOSTIC AND THERAPEUTIC METHOD FOR TUMOR USING RADIOLABELED AVIDIN

BACKGROUND OF THE INVENTION

1. Field of the Invention

The present invention relates to diagnosis and therapeutics of tumors of animal including human as well as a radioactive diagnostic and radioactive therapeutic agent useful for such purpose.

2. Background Arts

Pharmaceuticals in which a substance accumulating in tumor is bound to a radionuclide have been developed in order to diagnose tumor grown in body of animal including human.

Because of harmfulness of the radionuclides against cells, it is desirable that the pharmaceuticals do not accumulate in the normal region but are bound only to tumor cells, accumulating therein for a long period.

While therapeutics including systemic chemotherapy, intraperitoneal chemotherapy, beam radiotherapy, intracavitary radioactive colloid instillation and so on were attempted by Lacy et al. for therapeutics of intraperitoneal tumor (Lacy et al, Management of Malignant Ascites, Surg. Gynecol. Obstet., 159, 397–412, 1984), no approach has demonstrated sufficient efficacy.

Targeting therapeutics using anti-tumor monoclonal antibodies conjugated with radionuclides, chemotherapeutics or toxins could be highly specific to tumors, less toxic to normal cells and highly toxic to tumors. Particularly, attempts for therapeutics of intraperitoneal tumor with radiolabeled antibodies were found effective for animal patients including human. However, the administration of radioactive species for therapeutic purpose was limited because the blood radioactivity level and nonspecific uptake of radiolabeled substance into normal tissues were undesirably high.

It has been described by Lotan (R. Lotan, Lectins in Cancer Cells, Annals of New York Academy of Sciences, 551, 385–398, 1988) that lectins are present on the surface of tumor cell and that ligands bound to lectins are internalized by the cells. Lectins are proteins bound to saccharides, have two or more binding sites, agglutinate animal and plant cells, and precipitate polysaccharides and complex carbohydrates. Their binding specificity can be defined by inhibition test using monosacchrides and oligosaccharides, and various lectins have been known. It can be said that substances specifically recognizing lectins on a tumor surface are promising for tumor controlling but no effective substance has been reported showing sufficiently high uptake for allowing image processing.

In view of circumstances that no appropriate ligand has been found out in spite of expectation that ligands which can bind to lectins on a surface of tumor cells and can be internalized by the tumor cells from the tumor surface can be carriers useful in diagnosis and therapy of tumors, an object of the present invention is to find out ligands showing sufficiently high accumulation by binding to lectins and to provide radioactive diagnostic and therapeutic agents useful in diagnosis and therapeutics of tumors by binding radionuclides to said ligands.

In order to solve such problem, the present inventors have conducted extensive studies and have found out, as a result, glycoproteins having molecules capable of binding to lectins on a tumor surface, and successfully completed the present invention.

SUMMARY OF THE INVENTION

The present invention provides a method for diagnosis of tumor which comprises administering a measurable amount of a glycoprotein having a molecule capable of specifically binding to lectins to a subject in need of such diagnosis and measuring said glycoprotein in said subject.

Also, the present invention provides a method for therapeutics of tumor which comprises administering an effective amount of a glycoprotein having a molecule capable of specifically binding to lectins to a subject in need of such treatment.

Further, the present invention provides a diagnostic agent or therapeutic agent of tumor comprising a glycoprotein having a molecule capable of specifically binding to lectins, in association with a pharmaceutically acceptable carrier, diluent or excipient.

In one aspect, the glycoprotein has N-acetylglucosamine or mannose as the molecule capable of specifically binding to lectins, and preferably, avidin is used as the glycoprotein.

In another aspect, the glycoprotein as the active ingredient used in the method for diagnosis or preparation of diagnostic agent of the present invention (hereinafter, referred simply to as "diagnostic agent") has a radioactive label selected from the group consisting of In-111, Tc-99m and I-123.

In a further aspect, the glycoprotein as the active ingredient used in the method for therepeutics or preparation of the therapeutic agent of the present invention (hereinafter, referred simply to as "therapeutic agent") has a radioactive label selected from the group consisting of In-111, I-131 and I-125.

Figure 1:
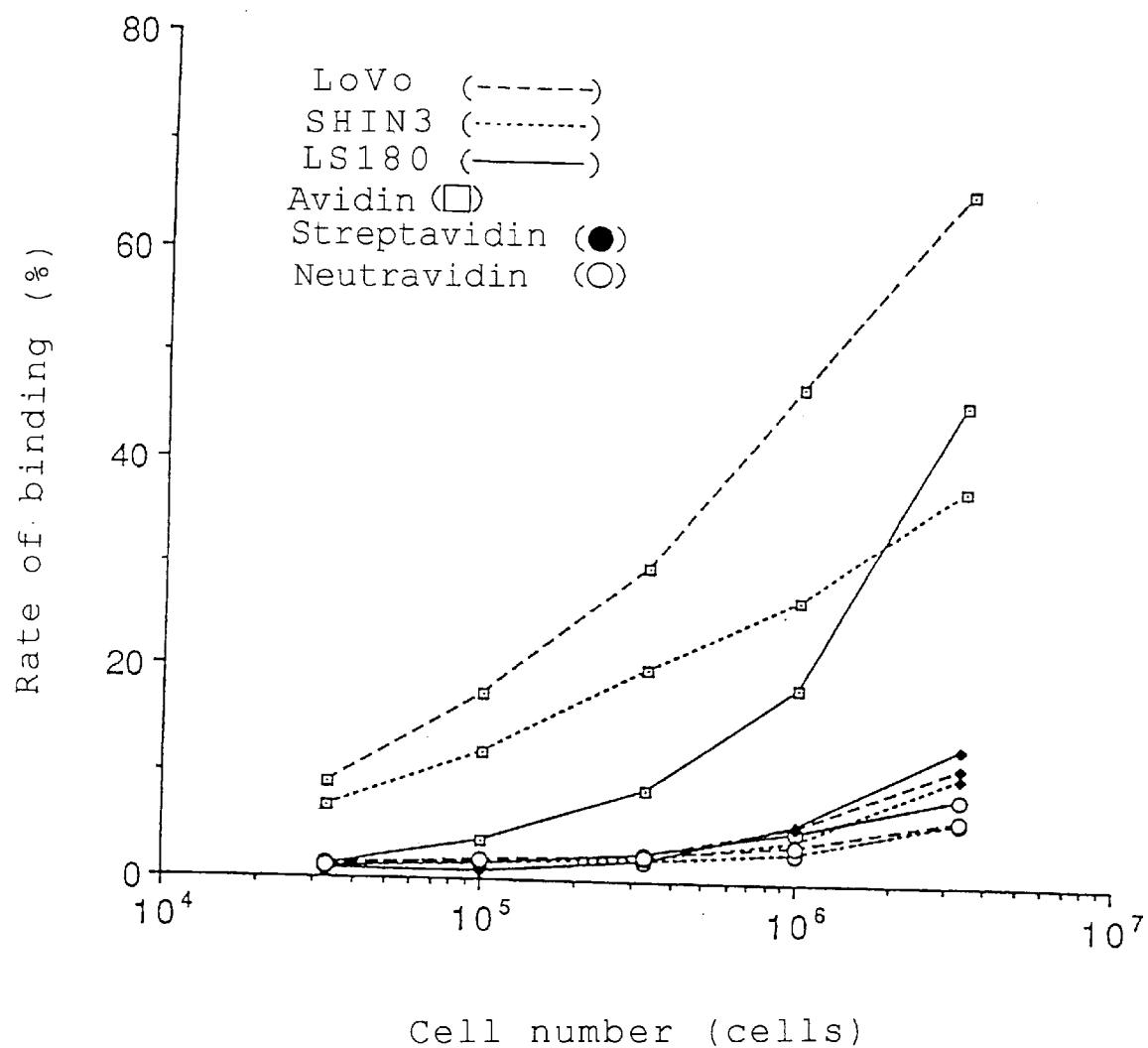
FIG. 1 is a graphic expression showing binding rate of avidin, streptavidin and neutravidin with tumor cells SHIN 3, LS 180 and LoVo in varied cell numbers.

In the drawings, SP denotes the spleen, I the intestine, L the liver, ST the stomach, K the kidney and T the tumor.

DETAILED DESCRIPTION

The diagnostic agent or therapeutic agent of the present invention comprises, as an active ingredient, a glycoprotein having a molecule capable of specifically binding to lectins. Particularly, the molecule capable of specifically binding to lectins is preferably terminal N-acetylglucosamine or mannose, and preferred glycoprotein is avidin which has the both and which is highly glycosylated.

Comparing uptake of avidin or avidin derivative into murine intraperitoneal tumor by in vitro experiments using streptavidin which has no sugar chain, neutravidin which has no carbohydrate and avidin which has both of N-acetylglucosamine and mannose, the uptake of avidin was the greatest and was 18.2–47.2%, while the uptake of streptavidin and neutravidin were 4–4.5% and 2.6–4.8%, respectively. It is considered, therefore, that avidin binds most strongly to lectins expressed on the surface of tumor cell.

Avidin is promising as a carrier in diagnostic or therapeutic products for radio isotopes, drugs or the like, if avidin bound to lectins is internalized by the tumor.

Therefore, the following experiment has been conducted using biotin which is employed in various biochemical experiments because of its known specific binding ability to avidin and of its dissociation constant as low as $10^{-15}$M (Y. Hiller et al., Biotin Binding to Avidin, Oligosaccharide Side Chain not Required for Ligand Association, Biochem. J., 248, 167–171, 1978).

When biotin is administered after administration of avidin in in vivo experiment, biotin shows similar accumulation to that of avidin-biotin conjugate if the administration of them is carried out within a short interval. This is because the first coming avidin binds to lectins on the tumor surface and the later coming biotin binds to avidin on the surface of tumor cell, showing as the result similar accumulation. As the interval between the administration of avidin and that of biotin becomes longer, biotin does not show the accumulation similar to avidin-biotin conjugate. This is considered to be due to the transfer of lectins bound to avidin into the inside of the tumor with the passage of time, resulting in failure of binding of biotin to avidin already internalized by the tumor, thus failing to show accumulation into the tumor. In such a manner, the property of avidin causing binding to lectins and being internalized by the tumor is very useful for the diagnostic agent and therapeutic agent of tumor.

The conjugate of avidin with a radionuclide can be obtained by binding a nuclide with avidin through intervention of a chelating agent, or by binding a radionuclide containing compound having a high reactivity with avidin, or by binding a conjugate of a radionuclide and biotin through intervention of a chelating agent with avidin.

Preferred nuclides used in the diagnostic agent include In-111, Tc-99m and In-123. Also usable are Cu-64, Ga-67 and others.

Preferred nuclides used in the therapeutic agent include In-111, I-131 and In-125. Also usable are H-3, C-14, Cu-67, Re-186, Re-188, Y-90 and others.

When biotin is labeled with In-111, the labeling can be performed by dissolving DTPA (diethylenetriaminepentaacetic acid)-bis(biocytinamide) in a buffer solution or the like and mixing the solution with a solution containing In-111 ion.

When biotin is labeled with Tc-99m, the labeling can be performed, according to a routine process, by dissolving DTPA (diethylenetriaminepentaacetic acid)bis (biocytinamide) in a buffer solution or the like, adding thereto a reducing agent having an appropriate redox potential such as stannous chloride and mixing the solution with a pertechnetate solution containing Tc-99m ion.

When avidin is labeled with I-131, the labeling can be performed by synthesizing N-succinimidyl 3-(tri-n-butylstanyl)benzoate according to the method, for example, described by Arano et al. (J. Med. Chem. 34, 2609–2618, 1994), binding it with I-131 by the halogen exchange reaction according to the method described by Zalutsky et al. (Zalutsky et al., Appl. Raiat. Isot., 38/12, 1051–1055, 1987) and then binding the product with avidin.

Binding of avidin or biotin with other radionuclides can suitably be effected using an appropriately selected exchange reaction or chelating compound.

When a conjugate with a radionuclide label is used as the radioactive diagnostic agent or the radioactive therapeutic agent, the labeled product prepared by the above-described process may be used after subjecting further to a purification step by HPLC method to remove impurity and unreacted indium ion, iodide ion or pertechnetate ion.

By intraperitoneally injecting a conjugate of radiolabeled biotin and avidin into a tumor-xenografted mouse and imaging by a gamma camera, uptake into the tumor could be observed between 2 and 24 hours. When the tumor organ was removed and imaged with a gamma camera, a high radioactivity level was observed in the tumor, indicating a result agreed with the data of biodistribution.

Tumor cells were intraperitoneally xenografted into mice, which were allotted to a group given with radiolabeled avidin and a group given with unlabeled avidin, and assayed for changes in the weight of tumor cells and of number of leukocyte. It could be found that, the weight of tumor cells was evidently decreased in the group of mice given with radiolabeled avidin as compared with the group of mice given with unlabeled avidin, but no significant decrease in the number of leukocyte was observed in both groups. Therefore, the therapeutic agent according to the present invention allows treatment of tumors without unnecessary destruction of leukocyte.

The conjugate with a radionuclide can be mixed with a pharmaceutically acceptable carrier to form a radioactive diagnostic agent or a radioactive therapeutic agent. Said carrier includes pharmaceutically acceptable stabilizers such as ascorbic acid, p-aminobenzoic acid and the like, pH adjusting agent such as aqueous buffer solution and the like, bulking agent such as D-mannitol and the like, and substances useful for improving radiochemical purity such as citric acid, tartaric acid, malonic acid, sodium gluconate, sodium glucoheptonate and the like. In addition, it is possible to provide the radioactive diagnostic agent or the radioactive therapeutic agent of the present invention in the form of a kit for preparation before use containing a conjugate and a carrier.

The radioactive diagnostic agent or the radioactive therapeutic agent of the present invention comprising a conjugate of a glycoprotein, preferably avidin or a derivative thereof, with a radionuclide can be administered by common parenteral route, for example, intraperitoneally, intrapleurally, by subcutaneous (local) injection, by intraarterial injection, by intravenous injection and so on. The amount of radioactivity which allows imaging and treatment can be decided taking various conditions including weight and age of patients, appropriate radio-imaging apparatus, condition of target disease and the like into consideration.

When the subject is human, the amount to be administered of the diagnostic agent containing a conjugate having a Tc-99m label lies within a range of 37 MBq–1110 MBq, preferably of 185 MBq–1110 MBq, expressed by radioactivity of Tc-99m. Similar range can be applied to a conjugate with I-123 or In-111.

In the case of the therapeutic agent using a compound labeled with I-131, the range is 37 MBq–3700 MBq, preferably 1110 MBq–3700 MBq, expressed by radioactivity of I-131.

EXAMPLES

Example 1

Establishment of Tumor Model

Cells from SHIN 3 (a cell line from ovarian cancer), LS 180, LoVo (cell lines from colon cancer) and AOI (a cell line from lung cancer) were cultured in RPMI 1640 medium with 10% fetal calf serum and 0.03% L-glutamic acid. Subconfluent cells were harvested using a calcium- and magnesium-free phosphate buffered saline (PBS) containing 0.02% EDTA. Upon injection of $3\times10^6$ LS 180 or LoVo, or 1×10⁷ SHIN 3 or AOI in 0.2 ml PBS into female BALB/C nu/nu mice, tumors were found after 11 to 25 days. The weights of tumors were 0.1 to 0.5 mg.

Example 2

Labeling of Biotin with In-111

Into 0.3 M Tris HCl buffer, pH 7.0, was dissolved 3 μg DTPA (diethylenetriaminepentaacetic acid)-bis (biocytinamide) and the mixture was incubated together with 18.5 MBq In-111 at room temperature for 30 minutes. Because over 99% of the radioactivity were bound to the immobilized avidin gel, the obtained In-111 labeled biotin was used without further purification.

Direct Labeling of Avidin with I-131

The labeled product was obtained by !synthesizing N-succinimidyl 3-(tri-n-butylstanyl)benzoate according to the method described by Arano et al. (J. Med. Chem. 34, 2609–2618, 1994), binding it with I-131 by the halogen exchange reaction according to the method described by Zalutsky et al. (Zalutsky et al., Appl. Raiat. Isot., 38/12, 1051–1055, 1987) and then binding the product with avidin.

Radioactivity Labeling of Avidin through Intervention of Biotin

Avidin, streptavidin and neutravidin were mixed with radiolabeled biotin at a molecular ratio of 3–10:1 and allowed to stand for 30 minutes to give a bound compound. Unbound radiolabeled biotin was removed by chromatography over PD10 column manufactured by Pharmacia.

Example 3

In vitro Reactivity

Reactivity of avidin, streptavidin and neutravidin against cells SHIN 3, LS 180 and LoVo established in Example 1 was studied. Radiolabeled avidin, streptavidin and neutravidin was incubated with one of several kinds of cell numbers in 100 μl phosphate buffer in a 5.7×46 mm small centrifuge tube for 1 hour. The mixture was centrifuged at 10,000×g and the supernatant was removed by suction. The rate of radioactivity bound to cells was measured with an auto-well gamma counter (ARC300. Manufactured by Aloka).

The results are shown in FIG. 1. From FIG. 1, it can be seen that avidin showed a clearly high binding ability against the xenografted tumor cell as compared with streptavidin and neutravidin.

Example 4

Biodistribution

Experiments for biodistribution were conducted in two manners including a process wherein avidin radiolabeled through intervention of biotin was administered (1 step process) and a process wherein avidin was first administered and then radiolabeled biotin followed (2 step process).

(1 Step Process)

Avidin, streptavidin or neutravidin, which was labeled with In-111 through intervention of biotin, was injected into tumor-xenografted mice obtained in Example 1. Biodistribution of radioactivity was measured on 4 or 5 mice at 2–24 hours. The results for avidin are shown in Table 1. From Table 1, it can be seen that avidin effectively accumulated in the tumor cells and rapidly disappeared from non-tumor tissues. For comparison purpose, Table 2 shows results of biodistribution after 2 hours from administration of avidin, streptavidin or neutravidin bound with radiolabeled biotin to tumor-xenografted mice using LS 180.

TABLE 1

Biodistribution of radiolabeled avidin in mice having intraperitoneally xenografted tumor.

| Passage of time after administration of tumor cell (hr) | SHIN3 | | AOI | |
|---|---|---|---|---|
| | 2 | 24 | 2 | 24 |
| Blood | 0.17 ± 0.10 | 0.14 ± 0.05 | 0.20 ± 0.10 | 0.13 ± 0.04 |
| Liver | 2.79 ± 0.36 | 5.51 ± 1.83 | 7.04 ± 3.63 | 3.39 ± 1.87 |
| Kidney | 3.62 ± 0.73 | 6.23 ± 1.87 | 8.97 ± 4.47 | 4.17 ± 1.94 |
| Intestine | 1.61 ± 0.77 | 0.55 ± 0.18 | 3.00 ± 1.59 | 1.05 ± 0.32 |
| Stomach | 4.81 ± 2.95 | 1.69 ± 0.54 | 7.23 ± 4.01 | 2.22 ± 0.70 |
| Spleen | 3.47 ± 1.26 | 4.25 ± 0.73 | 9.69 ± 3.36 | 4.53 ± 2.88 |
| Lung | 0.50 ± 0.27 | 2.22 ± 1.23 | 2.29 ± 1.64 | 0.82 ± 0.49 |
| Muscle | 0.08 ± 0.05 | 0.08 ± 0.02 | 0.11 ± 0.04 | 0.07 ± 0.02 |
| Bone | 0.31 ± 0.08 | 0.57 ± 0.13 | 0.49 ± 0.20 | 0.25 ± 0.02 |
| Tumor | 57.3 ± 10.8 | 58.3 ± 15.7 | 86.4 ± 35.0 | 51.4 ± 14.1 |
| Tumor/Blood | 433.2 ± 227 | 433.6 ± 122 | 493.0 ± 300 | 423.5 ± 80.9 |
| Tumor/Liver | 20.5 ± 2.18 | 10.8 ± 1.47 | 14.9 ± 7.14 | 17.3 ± 5.60 |
| Tumor/Kidney | 16.4 ± 4.41 | 9.47 ± 1.42 | 11.6 ± 5.54 | 13.4 ± 3.51 |
| Tumor/Intestine | 42.6 ± 19.5 | 108.7 ± 15.9 | 35.1 ± 19.1 | 52.7 ± 22.3 |
| Tumor/Bone | 191.7 ± 52.5 | 101.1 ± 10.2 | 199.6 ± 91.2 | 201.0 ± 41.9 |
| Passage of time after administration of tumor cell (hr) | LS180 | | LoVo | |
| | 2 | 24 | 2 | 24 |
| Blood | 0.23 ± 0.02 | 0.19 ± 0.11 | 0.21 ± 0.03 | 0.08 ± 0.03 |
| Liver | 18.4 ± 2.13 | 16.9 ± 3.89 | 14.3 ± 1.47 | 7.70 ± 6.73 |
| Kidney | 21.0 ± 2.03 | 19.1 ± 3.27 | 19.9 ± 3.14 | 7.11 ± 5.73 |
| Intestine | 1.65 ± 0.33 | 2.75 ± 0.42 | 1.33 ± 0.19 | 1.06 ± 0.68 |
| Stomach | 6.26 ± 3.21 | 2.82 ± 0.77 | 3.81 ± 1.07 | 3.31 ± 2.18 |
| Spleen | 13.5 ± 1.40 | 11.6 ± 1.33 | 11.9 ± 2.60 | 5.22 ± 4.68 |
| Lung | 1.63 ± 1.31 | 1.32 ± 0.34 | 0.84 ± 0.61 | 1.06 ± 0.99 |
| Muscle | 0.15 ± 0.05 | 0.14 ± 0.05 | 0.08 ± 0.02 | 0.14 ± 0.10 |
| Bone | 0.88 ± 0.12 | 0.91 ± 0.17 | 0.84 ± 0.24 | 0.55 ± 9.46 |

TABLE 1-continued

Biodistribution of radiolabeled avidin in mice having intraperitoneally xenografted tumor.

| | | | | |
|---|---|---|---|---|
| Tumor | 96.4 ± 31.2 | 65.7 ± 26.2 | 148.2 ± 27.7 | 68.2 ± 38.0 |
| Tumor/Blood | 428.4 ± 137 | 383.4 ± 163 | 719.3 ± 186 | 845.0 ± 168 |
| Tumor/Liver | 5.24 ± 1.67 | 4.26 ± 2.57 | 10.5 ± 2.87 | 13.4 ± 8.04 |
| Tumor/Kidney | 4.59 ± 1.38 | 3.62 ± 1.86 | 7.70 ± 2.36 | 12.4 ± 5.24 |
| Tumor/Intestine | 58.9 ± 19.1 | 24.5 ± 11.5 | 114.7 ± 35.6 | 69.1 ± 14.9 |
| Tumor/Bone | 108.3 ± 27.5 | 75.2 ± 36.7 | 186.0 ± 62.3 | 162.0 ± 78.8 |

(Each value represents mean ± standard deviation of the amount of radioactivity per 1 g of each organ from 4–5 mice, and a ratio between the values.)

TABLE 2

Biodistribution (after 2 hours from administration) of radiolabeled avidin, streptavidin and neutravidin in mice having intraperitoneally xenografted tumor (LS12).

| | Avidin | Streptavidin | Neutravidin |
|---|---|---|---|
| Blood | 0.23 ± 0.02 | 15.3 ± 1.57 | 9.43 ± 2.87 |
| Liver | 18.4 ± 2.13 | 4.45 ± 0.89 | 18.2 ± 5.15 |
| Kidney | 21.0 ± 2.03 | 21.2 ± 2.74 | 9.77 ± 3.28 |
| Intestine | 1.65 ± 0.33 | 3.30 ± 0.50 | 1.70 ± 0.20 |
| Stomach | 6.26 ± 3.21 | 1.83 ± 0.06 | 1.33 ± 0.81 |
| Spleen | 13.5 ± 1.40 | 3.49 ± 0.51 | 13.2 ± 5.45 |
| Lung | 1.63 ± 1.31 | 9.08 ± 1.67 | 3.35 ± 0.94 |
| Muscle | 0.15 ± 0.05 | 2.17 ± 0.36 | 2.05 ± 0.69 |
| Bone | 0.88 ± 0.12 | 2.17 ± 0.36 | 2.05 ± 0.69 |
| Tumor | 96.4 ± 31.2 | 10.2 ± 1.52 | 17.5 ± 4.59 |
| Tumor/Blood | 428.4 ± 137 | 0.67 ± 0.09 | 1.90 ± 0.22 |
| Tumor/Liver | 5.24 ± 1.67 | 2.36 ± 0.62 | 0.98 ± 0.20 |
| Tumor/Kidney | 4.59 ± 1.38 | 0.48 ± 0.06 | 1.88 ± 0.58 |
| Tumor/Intestine | 58.9 ± 19.1 | 3.10 ± 0.44 | 10.33 ± 2.64 |
| Tumor/Bone | 108.3 ± 27.5 | 4.74 ± 0.75 | 8.85 ± 2.37 |

Each value represents mean ± standard deviation of the amount of radioactivity per 1 g of each organ from 4–5 mice, and a ratio between the values.)

(2 Step Process)

LS 180-tumor xenografted mice received injection with 300 µg unlabeled avidin and 1–24 hours later injection with 0.3 µg In-111 labeled biotin. A group of LS 180-xenografted mice did not receive avidin but received In-111labeled biotin alone. After 2 hours from the injection of biotin, 4–5 mice per group were sacrificed and measured for distribution of radioactivity. The results are shown in Table 3. The radioactivity in the tumor decreased as the passage of time between the injection of avidin and administration of radiolabeled biotin became longer, for both of normal and tumor tissues. As shown later, effect of endogenous biotin was little. There was a possibility of internalization of avidin by the tumor cell, suggested by the fact that the distribution of biotin administered after 24 hours from the injection of avidin was similar to the distribution of biotin without administration of avidin in spite of specific binding of avidin to the tumor cell.

TABLE 3

Distribution of radioactivity after 2 hours from administration of biotin in the case where radiolabeled biotin was administered after pre-targeting of avidin to mice having intraperitoneally xenografted tumor (LS180)

| Passage of time after pre-targeting of avidin (hr) | 1 | 4 | 8 |
|---|---|---|---|
| Blood | 0.38 ± 0.08 | 0.25 ± 0.03 | 0.20 ± 0.03 |
| Liver | 14.77 ± 2.84 | 1.92 ± 0.58 | 0.21 ± 0.04 |
| Kidney | 17.44 ± 2.16 | 3.30 ± 0.94 | 1.41 ± 0.29 |

TABLE 3-continued

Distribution of radioactivity after 2 hours from administration of biotin in the case where radiolabeled biotin was administered after pre-targeting of avidin to mice having intraperitoneally xenografted tumor (LS180)

| Intestine | 1.03 ± 0.30 | 0.27 ± 0.06 | 0.11 ± 0.02 |
|---|---|---|---|
| Stomach | 3.24 ± 0.63 | 1.08 ± 0.44 | 0.13 ± 0.09 |
| Spleen | 12.85 ± 4.02 | 2.14 ± 1.24 | 0.26 ± 0.13 |
| Lung | 1.07 ± 0.91 | 0.32 ± 0.11 | 0.19 ± 0.10 |
| Muscle | 0.10 ± 0.06 | 0.32 ± 0.22 | 0.06 ± 0.03 |
| Bone | 0.99 ± 0.08 | 0.60 ± 0.45 | 0.20 ± 0.07 |
| Tumor | 59.28 ± 9.89 | 39.31 ± 11.3 | 10.49 ± 5.16 |
| Tumor/Blood | 160.3 ± 26.9 | 159.0 ± 50.9 | 52.6 ± 23.9 |
| Tumor/Liver | 4.19 ± 1.45 | 20.89 ± 5.43 | 48.14 ± 20.2 |
| Tumor/Kidney | 3.48 ± 0.94 | 12.26 ± 2.75 | 7.18 ± 2.66 |
| Tumor/Spleen | 5.14 ± 2.58 | 22.03 ± 9.18 | 40.87 ± 15.0 |
| Tumor/Bone | 60.7 ± 13.7 | 107.3 ± 79.1 | 59.22 ± 35.9 |

| Passage of time after pre-targeting of avidin (hr) | 24 | Without pre-targeting |
|---|---|---|
| Blood | 0.15 ± 0.07 | 0.12 ± 0.03 |
| Liver | 0.13 ± 0.02 | 0.17 ± 0.05 |
| Kidney | 1.01 ± 0.23 | 1.23 ± 0.21 |
| Intestine | 1.18 ± 1.35 | 0.49 ± 0.46 |
| Stomach | 1.49 ± 1.61 | 0.12 ± 0.03 |
| Spleen | 0.10 ± 0.01 | 0.18 ± 0.05 |
| Lung | 0.13 ± 0.06 | 0.14 ± 0.05 |
| Muscle | 0.12 ± 0.16 | 0.20 ± 0.27 |
| Bone | 0.17 ± 0.13 | 0.25 ± 0.34 |
| Tumor | 1.45 ± 0.70 | 0.70 ± 0.35 |
| Tumor/Blood | 9.72 ± 2.07 | 5.78 ± 2.44 |
| Tumor/Liver | 11.20 ± 3.77 | 3.90 ± 1.32 |
| Tumor/Kidney | 1.39 ± 0.40 | 0.55 ± 0.22 |
| Tumor/Spleen | 14.75 ± 5.59 | 3.94 ± 1.79 |
| Tumor/Bone | 9.42 ± 2.29 | 5.97 ± 3.51 |

(Each value represents mean ± standard deviation of the amount of radioactivity per 1 g of each organ from 4–5 mice, and a ratio between the values.)

Reference Example

Effect of Endogenous Biotin

Anti-human colon cancer monoclonal antibody MLS 128 was dissolved in phosphate buffer at a concentration of 5 mg/ml and incubated together with 9 µg NHS-LC-biotin (manufactured by Pierce) at 4° C. for 2 hours to give biotinylated antibody. Unbound biotin was removed by PD10 column manufactured by Pharmacia.

Biotin bound to the tumor cell even in the case where 300 µg biotinylated antibody was intraperitoneally pre-administered to tumor xenografted mice, 500 µg streptavidin was intraperitoneally administered and, 24 hours after, radiolabeled biotin antibody was administered. This indicates that effect of endogenous biotin is little.

Example 5

Scintigram

Figure 2:
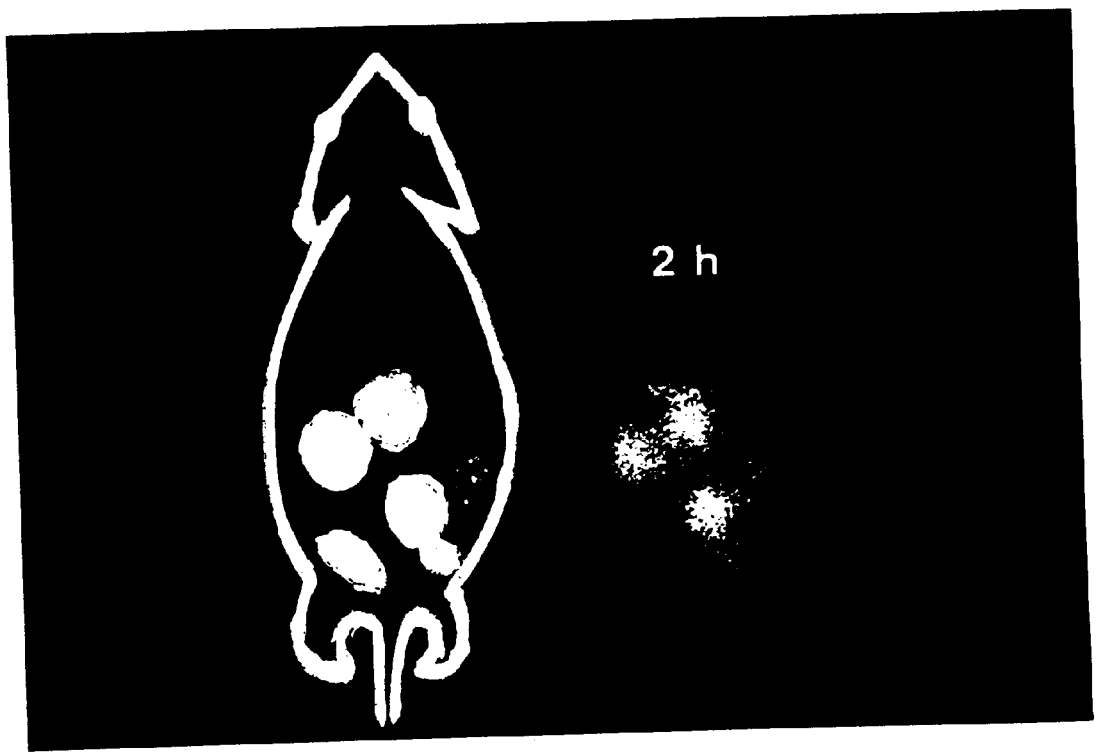
FIG. 2 is a photograph (morphology of organism) showing a scintigram of the body after 2 hours from the administration of avidin bound to biotin labeled with In-111 to a mouse xenografted with SHIN 3 tumor cells.
Figure 3:
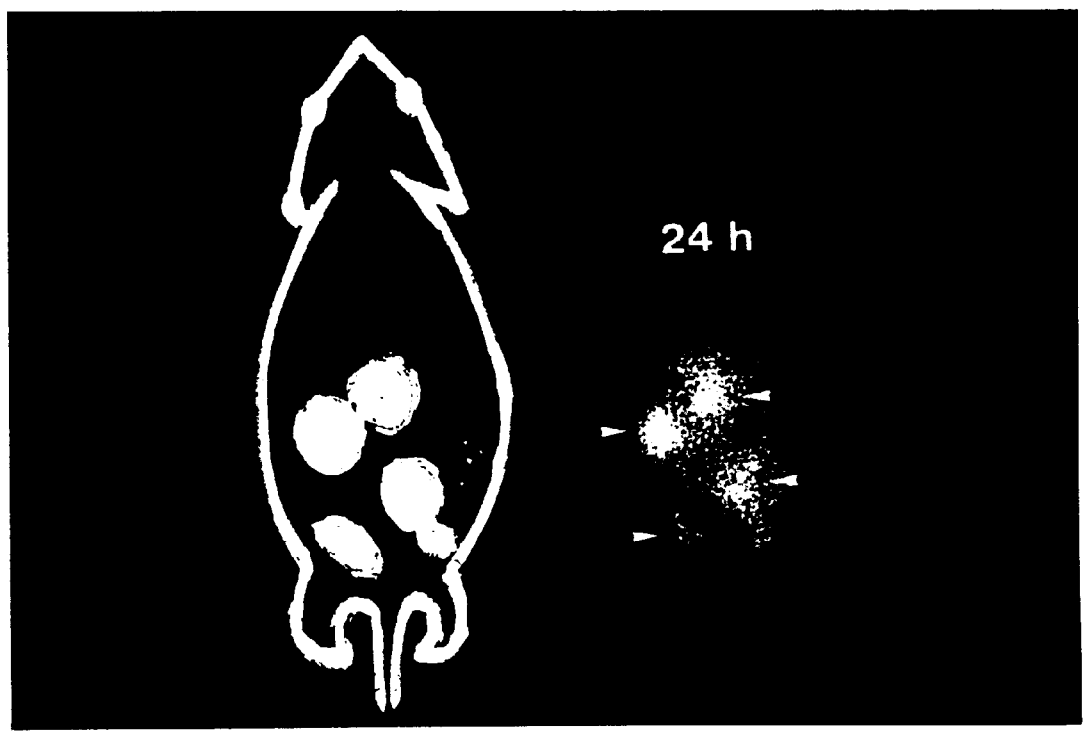
FIG. 3 is a photograph (morphology of organism) showing a scintigram of the body after 24 hours from the administration of avidin bound to biotin labeled with In-111 to a mouse xenografted with SHIN 3 tumor cells.
Figure 4:
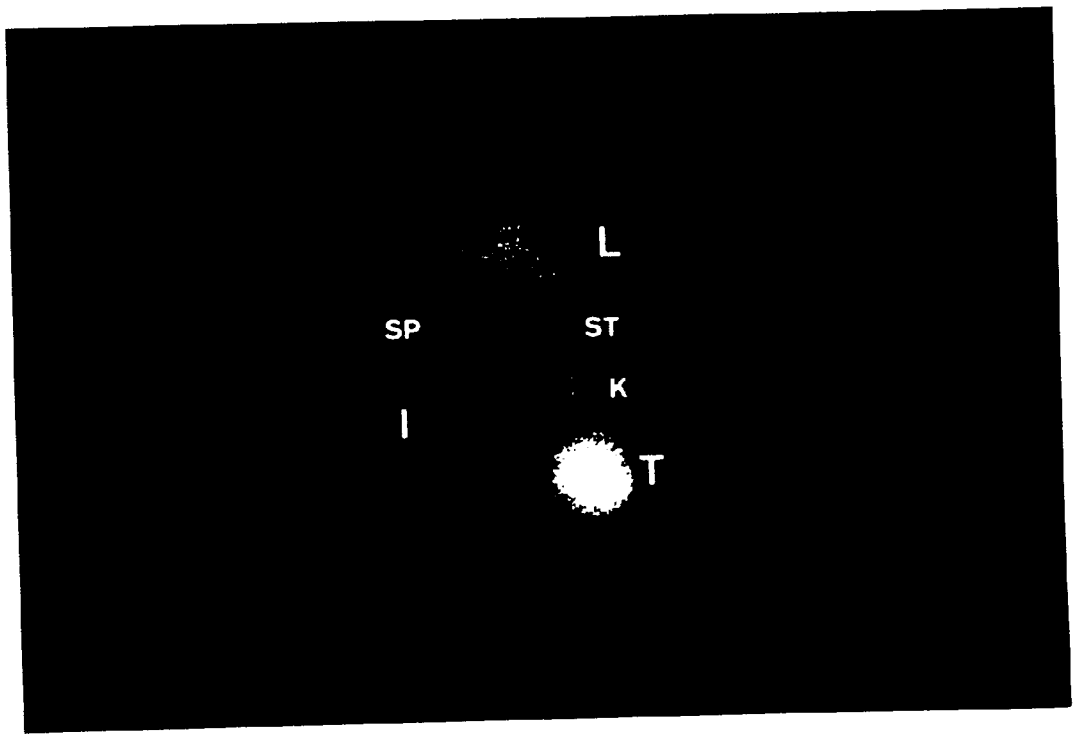
FIG. 4 is a photograph (morphology of organism) showing a scintigram of isolated organs after 24 hours from the administration of avidin bound to biotin labeled with In-111 to a mouse xenografted with SHIN 3 tumor cells.

For image analysis purpose, 3.7 µg radiolabeled avidin was intraperitoneally injected to SHIN 3-tumor xenografted mice. Images are shown in FIG. 2 and FIG. 3 that were obtained from anesthetized mice after 2 hours and 24 hours from the administration of avidin using a Searle gamma camera (PHO/GAMMA LFOB, manufactured by Searle Radiographics, Inc.) equipped with a pinhole collimeter. In addition, FIG. 5 shows a scintigram of removed organs put side by side. Good tumor accumulation was observed at both 2 hours and 24 hours. Further, accumulation of radioactivity in tumor was more clearly observed in the case of removed organs, indicating agreement with the biodistribution.

Example 6

Therapeutic Effect; Part 1

Nude mice were intraperitoneally treated with $1\times10^7$ SHIN 3 tumor cells and 2 days and 4 days later injected with 11.1 MBq and 9.25 MBq, respectively, of In-111 labeled avidin (100 μg). 13 and 18 days inoculation of tumor cells, mice were sacrificed and assayed for weight of tumor and number of leukocyte. For comparison purpose, mice were used which received the same amount of unlabeled avidin. The results are shown in Table4. Statistical analysis was made by t-test. The weight of tumor was clearly more reduced for the case where radiolabeled avidin was used as compared with the case where unlabeled avidin was used (level of significance: 0.02%). On the other hand, no difference was observed in the number of leukocyte, indicating that unnecessary destruction was not occurred (p-value: 0.3%).

TABLE 4

Weight of tumor and number of leukocyte in the case where In-111-avidin was administered.

| | 13 | | | 18 | | |
|---|---|---|---|---|---|---|
| Days after transplantation | Tumor (g) | (n) | Number of leukocyte (mm³) | Tumor (g) | (n) | Number of leukocyte (mm³) |
| Treated | 0.078 | (11) | 2386 | 0.161 | (8) | 3788 |
| Untreated | 0.391 | (10) | 3549 | 0.824 | (7) | 3,891 |
| p-value | <0.0001 | | 0.0032 | 0.0002 | | >0.2 |

Example 7

Therapeutic Effect; Part 2

Nude mice were intraperitoneally treated with $1\times10^7$ SHIN 3 tumor cells and 2 days and 7 days later injected with 11.1 MBq of I-131 labeled avidin (100 μg). Uptakes of radioactivity into the tumor or blood after 30 minutes and 24 hours were 45.8 or 0.71% ID/g and 15.2 or 0.05% ID/g, respectively. 18 days post-inoculation of tumor cells mice were sacrificed and assayed for weight of tumor. For comparison purpose, mice were used which received the same amount of unlabeled avidin. The results are shown in Table 5. Statistical analysis was made by t-test. The weight of tumor was clearly more reduced for the case where radiolabeled avidin was used as compared with the case where unlabeled avidin was used (p-value: 3%).

TABLE 5

Weight of tumor cells 18 days after intraperitoneal xenografting of the tumor cells into mice

| Days* | Treated (n) | Untreated (n) | p-value |
|---|---|---|---|
| 2 | 0.579 (9) | 0.926 (6) | 0.033 |
| 7 | 0.418 (8) | 0.845 (7) | 0.014 |

*Days represent time lapsed after the intraperitoneal xenografting until the treatment with I-131-avidin.

Because ingredients harmful not only to tumor cells but also to normal cells are used in the treatment of tumors, demands have existed for drugs having high specificity to tumors. Since the substances having avidin or having a lectin binding site of avidin according to the present invention have high specificity to lectin present on the tumor surface, they enable tumor-targeting treatment by binding with a radioactive substance and are useful in imaging of tumorous region by its high targeting ability.

What is claimed is:

1. A method for tumor diagnosis which consists of administering to a subject in need of such diagnosis a conjugate which consists of radiolabeled avidin, whereby said avidin directly binds lo a lectin present on the surface of said tumor and detecting said avidin bound to said tumor.

2. The method according to claim 1, wherein said radioactive label is a label selected from the group consisting of In-111, Tc-99m and I-123.

3. A method for treatment of a tumor which consists of administering to a patient in need thereof a conjugate which consists of a radiolabeled avidin, whereby said avidin directly binds to a lectin present on the surface of said tumor.

4. The method according to claim 3, wherein the radioactive label is a label selected from the group consisting of In-111, I-131 and I-125.

* * * * *